(12) United States Patent
Chu (10) Patent No.: US 10,792,062 B2
(45) Date of Patent: Oct. 6, 2020

(54) MEDICAL DEVICE HANDLES AND RELATED METHODS

(71) Applicant: Boston Scientific Scimed, Inc., Maple Grove, MN (US)

(72) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 214 days.

(21) Appl. No.: 15/842,308

(22) Filed: Dec. 14, 2017

(65) Prior Publication Data

US 2018/0168672 A1 Jun. 21, 2018

Related U.S. Application Data

(60) Provisional application No. 62/435,101, filed on Dec. 16, 2016.

(51) Int. Cl.
| | |
|---|---|
| A61B 17/29 | (2006.01) |
| A61B 17/221 | (2006.01) |
| A61B 1/00 | (2006.01) |
| A61B 17/16 | (2006.01) |
| A61B 90/00 | (2016.01) |

(Continued)

(52) U.S. Cl.
CPC ...... *A61B 17/2909* (2013.01); *A61B 1/00133* (2013.01); *A61B 17/1608* (2013.01); *A61B 17/221* (2013.01); *A61B 2017/0034* (2013.01); *A61B 2017/00367* (2013.01); *A61B 2017/00389* (2013.01); *A61B 2017/22074* (2013.01); *A61B 2017/2927* (2013.01); *A61B 2017/2946* (2013.01); *A61B 2090/0811* (2016.02)

(58) Field of Classification Search
CPC .......... A61B 17/221; A61B 2017/0034; A61B 2017/00389; A61B 2017/22074; A61B 2018/0091; A61B 2018/1407; A61B 2018/141; A61B 17/2909; A61B 17/32056; A61B 2017/2212; A61B 2017/291; A61B 2017/2911; A61M 5/3271; A61M 5/3272; A61M 2025/018
See application file for complete search history.

(56) References Cited

U.S. PATENT DOCUMENTS 4,718,419 A * 1/1988 Okada .............. A61B 17/32056
606/39
5,843,091 A 12/1998 Holsinger et al.
(Continued)

OTHER PUBLICATIONS

Notification of Transmittal of the International Search Report and the Written Opinion of the International Searching Authority, or the Declaration dated Feb. 27, 2018, in International Application No. PCT/US2017/066454 (13 pages).

*Primary Examiner* — Martin T Ton
(74) *Attorney, Agent, or Firm* — Bookoff McAndrews, PLLC (57) ABSTRACT

A medical device includes a sheath, an shaft at least partially surrounded by the sheath, an end effector at a distal end of the shaft and movable between at least an open position and a closed position, and a handle. The handle includes a shaft advancement body, a channel body securely coupled to the sheath and selectively positionable with respect to the shaft advancement body, and a plunger securely coupled to the shaft and selectively positionable with respect to the channel body.

17 Claims, 4 Drawing Sheets

(51) Int. Cl.
*A61B 17/00* (2006.01)
*A61B 17/22* (2006.01)

(56) References Cited

U.S. PATENT DOCUMENTS

| | | | |
|---|---|---|---|
| 5,971,994 A | 10/1999 | Fritzsch | |
| 2003/0120218 A1 | 6/2003 | Asbaghi | |
| 2003/0125731 A1* | 7/2003 | Smith | A61B 17/2909 606/47 |
| 2004/0171967 A1 | 9/2004 | Burbank et al. | |
| 2009/0030380 A1* | 1/2009 | Binmoeller | A61B 1/018 604/264 |
| 2010/0094216 A1* | 4/2010 | Yue | A61M 5/46 604/117 |
| 2014/0309655 A1* | 10/2014 | Gal | A61B 90/37 606/127 |
| 2014/0316203 A1* | 10/2014 | Carroux | A61B 17/221 600/146 |
| 2015/0164522 A1* | 6/2015 | Budiman | A61B 17/221 606/113 |
| 2016/0038174 A1* | 2/2016 | Bruzzi | A61B 17/221 606/159 |

\* cited by examiner

MEDICAL DEVICE HANDLES AND RELATED METHODS

CROSS-REFERENCE TO RELATED APPLICATIONS

This application claims the benefit of priority to U.S. Provisional Application No. 62/435,101, filed Dec. 16, 2016, which is incorporated by reference herein in its entirety.

TECHNICAL FIELD

Various aspects of the present disclosure relate generally to medical device handles and related methods. More specifically, the present disclosure relates to medical devices and medical device handles for selectively extending and retracting an end effector.

BACKGROUND

Medical devices, such as expandable baskets, retrieval devices, and the like may include a shaft arranged for delivery through a working channel of an endoscope device. The shaft of such medical devices may be selectively extended and retracted relative to the working channel of the insertion device or the device's sheath to deploy or retract the shaft to perform one or more therapies, treatments, or diagnostic evaluations on a subject. For example, the medical device may include a shaft that terminates distally at an end effector or an expandable basket. However, manipulating the shaft while delivering medical treatment may be cumbersome or difficult for the user or users. Such efforts may increase the length, cost, and/or complexity of the medical procedure.

The devices and methods of the current disclosure may rectify some of the deficiencies described above or address other aspects of the prior art.

SUMMARY

Examples of the present disclosure relate to, among other things, medical retrieval devices. Each of the examples disclosed herein may include one or more of the features described in connection with any of the other disclosed examples.

In one example, a medical device may include a sheath; an shaft at least partially surrounded by the sheath; an end effector at a distal end of the shaft and movable between at least an open position and a closed position; and a handle, the handle including: a shaft advancement body; a channel body securely coupled to the sheath and selectively positionable with respect to the shaft advancement body; and a plunger securely coupled to the shaft and selectively positionable with respect to the channel body.

The medical device may further include one or more of the following features. The channel body may include a channel pin that is movable within a slot in the shaft advancement body. The slot in the shaft advancement body may include at least one tab. The channel pin may be movable within the at least one tab of the slot to secure the channel body in a selected position in the shaft advancement body. The position of the channel pin with respect to the shaft advancement body may correlate a position of the channel pin with a position of the sheath. The plunger may include a plunger pin that is movable within a channel in the channel body to move the end effector relative to the sheath between the open position and the closed position. The channel may include a channel track and at least one channel tab extending from the channel track. The channel may further include a channel slot and a channel release slot. The plunger pin may be movable within the at least one channel tab and channel slot to secure the plunger in a selected position in the channel body. The movement of the plunger within the channel body may be urged proximally by a biasing member. The biasing member may be a compression spring. The shaft advancement body and the channel body may both include two radially opposing sides, and the two radially opposing sides may be mirror images. The end effector may include an expandable retrieval basket. The handle may further comprise a cap at a distal portion of the handle; and the cap may be internally threaded to form a seal when coupled to a port of an insertion device. The channel body may further include a radially extending knob at a proximal end; and the plunger may further include a radially extending plunger knob at a proximal end.

In another example, a system may include an insertion device including a body and a delivery shaft with a distal end, wherein the body includes a port and a deflection lever; and a medical device including a handle and an shaft at least partially surrounded by a sheath; wherein the handle includes a first member, a second member, and a plunger movable relative to one another, the shaft and sheath being controllably movable together and relative to one another when the medical device is coupled to the insertion device.

The system may further include one or more of the following features. The shaft and the sheath each may have lengths such that when the handle is coupled to the port of the insertion device, the shaft and the sheath are both generally flush with the distal end of the delivery shaft. The second member may be movable relative to the first member to extend the shaft and the sheath from the distal end of the delivery shaft. The plunger may be movable and/or rotatable relative to the second member to extend and/or rotate the shaft from the sheath.

In another example, a method for controlling movement of a medical device, the medical device including a handle, a sheath, a shaft, and an end effector, wherein the handle includes a first member, a second member, and a pusher member, may include: moving the sheath, the shaft, and the end effector relative to the first member; and moving the shaft and the end effector relative to the first member and the second member.

The method for controlling movement of a medical device may further include one or more of the following features. Manipulating the second member may move the sheath, the shaft, and end effector relative to the first member. Manipulating the pusher member may move the shaft and the end effector relative the first member and the second member.

Both the foregoing general description and the following detailed description are exemplary and explanatory only and are not restrictive of the features, as claimed. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal."

BRIEF DESCRIPTION OF THE DRAWINGS

The accompanying drawings, which are incorporated in and constitute a part of this specification, illustrate exemplary features of the present disclosure and together with the description, serve to explain the principles of the disclosure.

DETAILED DESCRIPTION

Examples of the present disclosure relate to medical device handles for deployment of a shaft of a medical device. The medical device may be delivered through any appropriate insertion device or alone through a bodily orifice, and the shaft may include any type of end effector or retrieval device, such as, e.g., a retrieval basket.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to an operator using the medical device or insertion device. In contrast, "distal" refers to a position relatively further away from the operator using the medical device or insertion device, or closer to the interior of the body.

Figure 1:
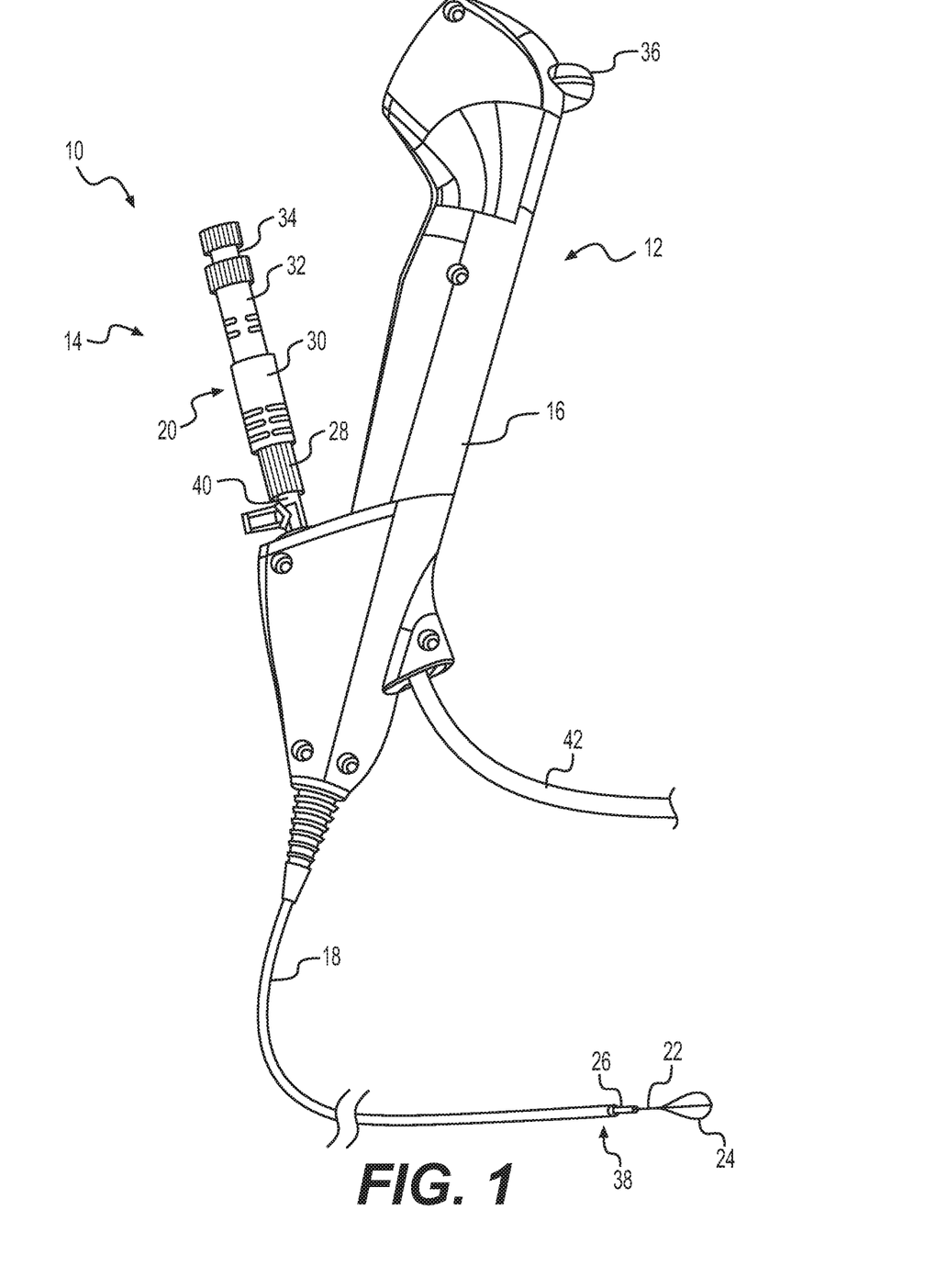
FIG. 1 illustrates an exemplary medical device coupled to an insertion device.

FIG. 1 illustrates a medical system 10, including an insertion device 12 and a medical device 14. Insertion device 12 may include a body 16 and a delivery shaft 18. Medical device 14 may include a handle 20 and a shaft 22 terminating distally at an end effector 24. Shaft 22 may be at least partially surrounded by a sheath 26. Handle 20 may include a cap 28, a first member or a shaft advancement body 30, a second member or a channel body 32, and a plunger 34. Shaft 22 may be connected to plunger 34, and sheath 26 may be connected to channel body 32.

Medical device 14 will be described as a retrieval basket device; however, it is understood that medical device 14 may be any type of medical device used in conjunction with insertion device 12 to delivery medical therapy to a target site inside a subject. For example, medical device 14 may alternatively be a laser fiber, an irrigation and/or aspiration tube, a snare, forceps, and/or a needle type device.

Insertion device 12 may be a ureteroscope (e.g., Lithovue™ Single-Use Digital Flexible Ureteroscope by Boston Scientific Corp.), a hysteroscope, a bronchoscope, a cystoscope, or any similar endoscope device. Insertion device 12 may include a deflection lever 36 to deflect a distal end 38 of the delivery shaft 18. Insertion device 12 may also include at least one port 40. The at least one port 40 may include a T-connector as shown in FIG. 1, a Y-connector, or another appropriate connector. Port 40 may be threaded or may be a female luer. The at least one port 40 may connect to a proximal end of the delivery shaft 18 through at least one internal lumen (not shown) in the body 16 of insertion device 12. Though not shown, insertion device 12 may include an integral camera at the distal end 38 that is connected to processing software and a display via a communication and power conduit 42.

Handle 20 of medical device 14 may be coupled to insertion device 12 by attaching cap 28 to port 40. Cap 28 may have a generally circular cross-section and also include an axial lumen through which shaft 22 and sheath 26 may pass through. Cap 28 may include a radially inward facing threading (not shown) on a portion of cap 28 that is radially external to the axial lumen to secure handle 20 to port 40. Cap 28 may further include an internal seal (not shown) surrounding the shaft 22 and sheath 26. Alternatively, cap 28 may be a rotating or non-rotating male luer, and port 40 may be a female luer. Cap 28 may include a ridged radially outer surface portion such that cap 28 may be gripped and manipulated longitudinally and rotationally by, for example, a user's fingers.

Figure 2:
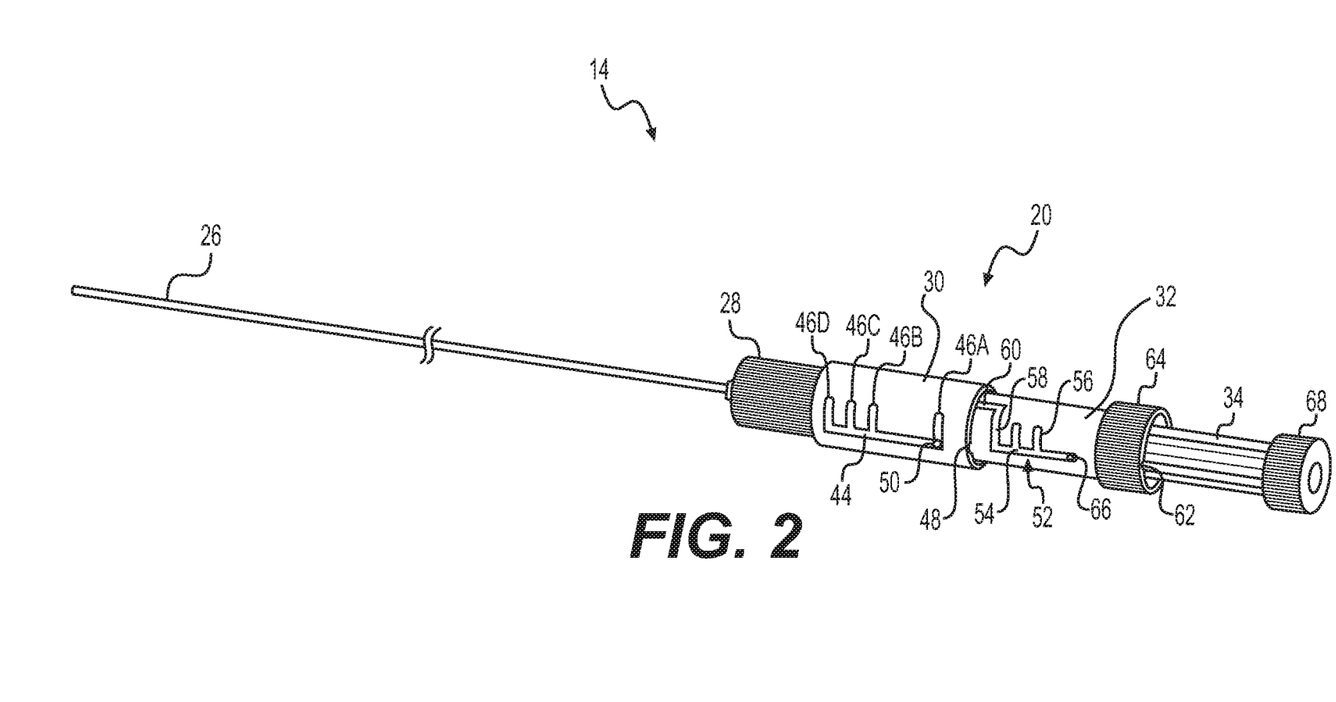
FIG. 2 illustrates a perspective view of the exemplary medical device of FIG. 1.

As shown in FIG. 2, shaft advancement body 30 is securely attached to a proximal end of cap 28 such that the shaft advancement body 30 is immovably attached to the proximal end of cap 28. Shaft advancement body 30 and cap 28 may also be integrally formed. Shaft advancement body 30 includes a generally circular cross-section with an axial lumen through which channel body 32 may be received and axially move. Shaft advancement body 30 also includes a longitudinally extending slot track 44 from which at least one tab 46 circumferentially extends. In one example, shaft advancement body 30 includes a plurality of tabs 46, and the tabs 46 may be constantly spaced and/or unevenly spaced. The tabs 46 may be uniformly sized, or may be different sizes to form different configurations. In one embodiment shown in FIG. 2, shaft advancement body 30 may include one distal tab 46A and three proximal tabs 46B, 46C, and 46D.

Though not shown, shaft advancement body 30 may include a mirror slot track and tabs on a circumferentially opposite side of shaft advancement body 30.

Shaft advancement body 30 may also feature at least one ramp 48 on a radially internal facing proximal portion. The at least one ramp 48 may be formed by a gradual decrease in thickness over a portion of the inner wall of shaft advancement body 30, and the at least one ramp 48 may be aligned with slot track 44.

Channel body 32 may be generally cylindrical and may be securely coupled to sheath 26. Channel body 32 may slide through the axial lumen of shaft advancement body 30 to control the distal positioning of shaft 22 and sheath 26, as shown in FIG. 2.

Channel body 32 includes at least one protrusion or pin 50 and a channel 52. Pin 50 may be formed by a cantilevered protrusion extending radially from channel body 32. Channel body 32 may be introduced into shaft advancement body 30 with pin 50 sliding through ramp 48 and into slot track 44. In use, pin 50 may be movable within slot track 44 and the tabs 46A-D, and may be frictionally secured within the tabs 46A-D.

Channel 52 may include a longitudinally extending channel track 54, at least one circumferentially extending channel tab 56 (two shown in FIG. 2), a channel slot 58, and a channel release slot 60. The at least one channel tab 56 and channel slot 58 may extend circumferentially and be perpendicular to channel track 54. Channel slot 58 may extend approximately 90° around the circumference of channel body 32, and channel release slot 60 may be parallel to channel track 54.

Channel body 32 may feature at least one channel ramp 62 on a radially internal facing proximal portion. The at least one channel ramp 62 may be formed by a gradual decrease in thickness over a portion of the inner wall of channel body 32, and the at least one channel ramp 62 may be circumferentially aligned with channel track 54.

Channel body 32 may also include a channel knob 64 at a proximal portion of channel body 32. Channel knob 64 may have a ridged outer surface such that channel knob 64 may be gripped by, for example, a user's fingers to longitudinally and rotationally manipulate channel body 32. In use, longitudinal and rotational manipulation of channel body 32 through channel knob 64 controls the position of pin 50 within slot track 44 and the at least one tab 46 of shaft advancement body 30, and thus also controls the distal positioning of shaft 22 and sheath 26 relative to distal end 38 of delivery shaft 18 of insertion device 12.

Although not shown, channel body 32 may include an additional pin and channel that mirror pin 50 and channel 52 on an opposite side of channel body 32.

Plunger 34 may be generally cylindrical and may be securely coupled to shaft 22. Plunger 34 may slide through an axial lumen of channel body 32 to control the distal positioning of shaft 22 relative to sheath 26. Plunger 34 includes a plunger pin 66. Plunger pin 66 may be formed by a cantilevered protrusion extending radially from plunger 34. Plunger 34 may be introduced into channel body 32 with plunger pin 66 sliding through channel ramp 62 and into channel track 54. In use, plunger pin 66 may be movable within channel 52.

Plunger 34 may also include a plunger knob 68 in a proximal portion of plunger 34. Plunger knob 68 may have a ridged outer surface such that plunger knob 68 may be gripped by, for example, a user's fingers to longitudinally and rotationally manipulate plunger 34. In use, longitudinal and rotational manipulation of plunger 34 through plunger knob 38 controls the position of plunger pin 66 within channel 52 of channel body 32, and thus also controls the distal positioning of shaft 22 relative to sheath 26. If shaft 22 has a self-expanding basket as end effector 24, the expandable basket expands as it extends from sheath 26 and delivery shaft 18. The channel 52 of channel body 32, including channel track 54, channel tabs 56, channel slot 58, and channel release slot 60, controls the longitudinal and rotational adjustments that a user may impart to the shaft 22 and end effector 24.

Although not shown, plunger 34 may include an additional plunger pin that mirrors plunger pin 64 on an opposite side of plunger 34 and is received in a mirror channel of channel 52.

Figure 3:
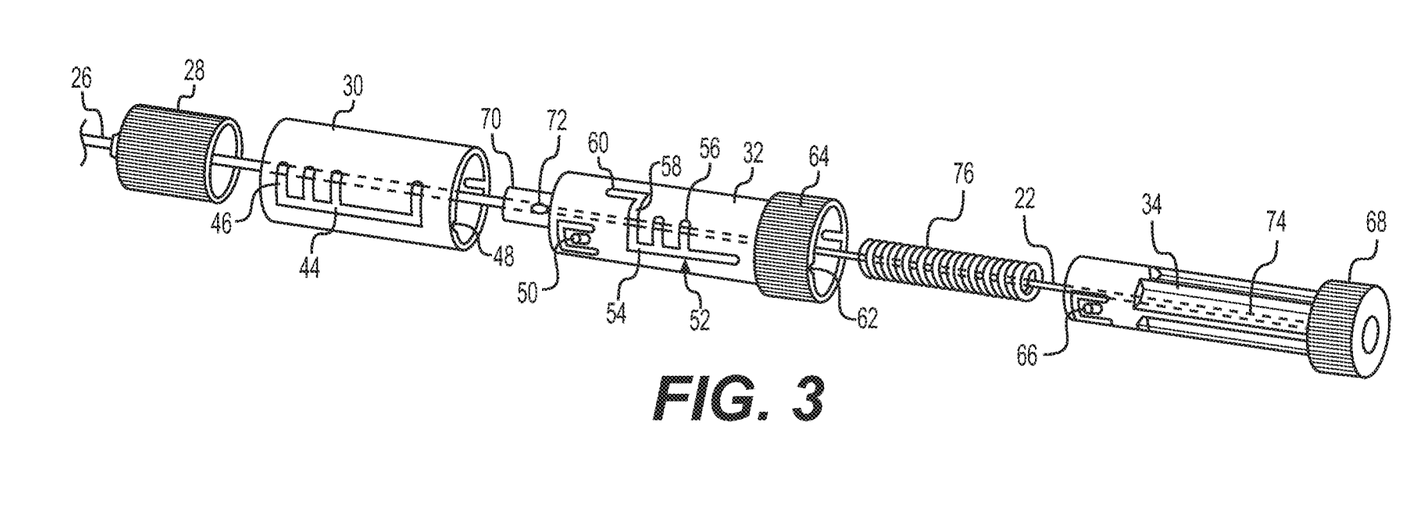
FIG. 3 illustrates an exploded view of medical device of FIG. 1.

FIG. 3 is an exploded view of the medical device 14. As shown, a narrowed distal portion 70 of channel body 32 may include an axial lumen and a hole 72. Shaft 22 may be movable within the axial lumen and sheath 26, but sheath 26 may be securely coupled to narrowed distal portion 70 of channel body 32. In one example, sheath 26 may be secured to narrowed distal portion 70 of channel body 32 by an adhesive through hole 72.

Furthermore, plunger 34 may also include a plunger lumen 74 that may receive and surround shaft 22. Shaft 22 may be securely coupled to a proximal portion of plunger 34 in any appropriate manner.

Channel body 32 may also enclose a biasing member 76. Biasing member 76 may be a spiral (compression) spring or any other suitable biasing element. Biasing member 76 may be positioned surrounding shaft 22. Biasing member 76 may be compressible between the proximal end of narrowed distal portion 70 of channel body 32 and a distal end of plunger 34. Biasing member 76 may bias the longitudinal movement of plunger 34 within the axial lumen of channel body 32 to urge the plunger proximally with respect to the channel body 32. The length and spring constant of biasing member 76 may be selectively chosen to provide the desired biasing force.

As shown in FIG. 1, medical device 14 may be introduced into insertion device 12 through port 40, and cap 28 may be coupled to port 40. In one aspect, medical device 14 may be quickly introduced into insertion device using an introducer sheath (not shown). Pin 50 and plunger pin 66 may have been introduced through ramp 48 and channel ramp 62 and positioned in the most proximal sections of slot track 44 and channel 52, respectively. Shaft 22 and sheath 26 may have a length such that with cap 28 fully mounted on port 40, shaft 22 and sheath 26 are either retracted slightly proximal to, generally flush with, or extended slightly distal to distal end 38 of delivery shaft 18 such that action on plunger 34 extends shaft 22 and end effector 24. Generally flush with shall be interpreted as within +/−5% of the length of the delivery shaft 18.

In one example, shaft 22 and sheath 26 are slightly proximal to distal end 38 of delivery shaft 18 when cap 28 is fully mounted on port 40 and pin 50 and plunger pin 66 are in their respective proximal most positions. A user may deflect the distal end 38 of delivery shaft 18 through action on deflection lever 36, with shaft 22 and sheath 26 protected within the delivery shaft 18.

Then, once the distal end 38 is proximate to the target material, the user may extend both the shaft 22 and sheath 26 from the distal end 38 of the delivery shaft 18 by gripping the channel knob 64 and manipulating channel body 32 to move distally within shaft advancement body 30. The same manipulation allows a user to move pin 50 within slot track 44 and position pin 50 within one of the at least one tabs 46A-D and thus frictionally secure the longitudinal position of the shaft 22 and sheath 26 relative to distal end 38. The plurality of tabs 46 connected by slot track 44 provide a user with a plurality of longitudinal positions in which to secure pin 50. As a result, a user may position the shaft 22 and sheath 26 in a plurality of positions relative to the distal end 38 of the delivery shaft 18. In another example, shaft advancement body 30 may include markings to correlate a position of the pin 50 in the plurality of tabs 46 with a corresponding position of the shaft 22 and sheath 26 relative to distal end 38.

Once the shaft 22 and sheath 26 are positioned, a user may extend the shaft 22 from sheath 26 through action on plunger 34. Distal force on plunger 34 pushes plunger 34 distally within channel body 32 and moves plunger pin 66 within channel 52. As discussed, end effector 24 of shaft 22 may be a self-expendable basket that expands as shaft 22 extends from sheath 26. A user may position plunger pin 66 within channel 52 to control the extension and expansion of the end effector 24 to capture the target material. For example, referring to FIG. 2, plunger pin 66 may be positioned in one of channel tabs 56, wherein positioning in a more distal tab extends the end effector 24 more distal from sheath 26. Alternatively, with shaft 22 and sheath 26 positioned flush with distal end 38 of delivery shaft 18, a user may extend the shaft 22 from sheath 26 without previously extending shaft 22 and sheath 26 from the distal end 38 of delivery shaft 18.

Positioning plunger pin 66 in one of channel tabs 56 biasingly secures plunger pin 66 and prevents biasing member 76 from proximally pushing plunger 34, and thus shaft 22, proximally. Furthermore, plunger pin 66 may be positioned in channel slot 58 to fully extend end effector 24 and capture target material. Plunger 34 may also be rotated to move plunger pin 66 within channel slot 58, and thus rotate shaft 22 and end effector 24. Additional distal force on plunger 34 may slide plunger pin 66 into channel release slot 60, causing end effector 32 to further expand and help release of captured target material that may be too large. Then, plunger 34 may be positioned such that plunger pin 66 is in channel track 54, so biasing member 76 biases plunger pin 66 proximally in the absence of distal force on plunger, thus retracting shaft 22 and end effector 24 into sheath 26. Moreover, channel body 32 may include markings to correlate a position of the plunger pin 66 in channel 52 with a corresponding position of the shaft 22 relative to the sheath 26.

The aforementioned steps may be repeated if retrieval of the target material was unsuccessful. Moreover, shaft 22 and sheath 26 may be retracted into distal end 38 of delivery shaft 18, and distal end 38 may be repositioned to a different position via deflection lever 36 without risking damage to the end effector 24 before repeating the retrieval steps if, for example, the target material moved. If successful, end effector 24 and shaft 22 may be retracted within sheath 26 by manipulating plunger 34 to move plunger pin 66 proximally within channel 52. Sheath 26, enclosing end effector 24, shaft 22, and any captured material, may be retracted proximally beyond distal end 38 of delivery shaft 18 by manipulating channel body 32 to move pin 50 proximally within slot track 44. Then, medical device 14 may be removed from a subject by uncoupling cap 28 from port 40, or medical device 14 may be removed from a subject together with insertion device 12.

Alternatively, though not illustrated, medical device 14 may include an additional biasing member to bias movement of channel body 32 relative to shaft advancement body 30 in a similar manner as that explained above with respect to biasing member 76. Shaft advancement body 30 may also be clear or transparent such that a user may see the position of plunger pin 66 in channel 52 even when channel body 32 is fully enclosed by shaft advancement body 30. Moreover, it is noted that the force required to uncouple cap 28 from port 40 may be a greater rotational force than the rotational force required to rotate pin 50 and/or plunger pin 66.

Different end effectors 24 may dictate the arrangement of channel 52. For example, a zero-tip expandable basket may be useful with a channel 52 having only a proximal channel tab and a distal channel tab, while a hybrid expandable basket may be useful with a channel 52 having a series of channel tabs to open the basket to varying configurations, as shown in FIGS. 2 and 3.

Figure 4:
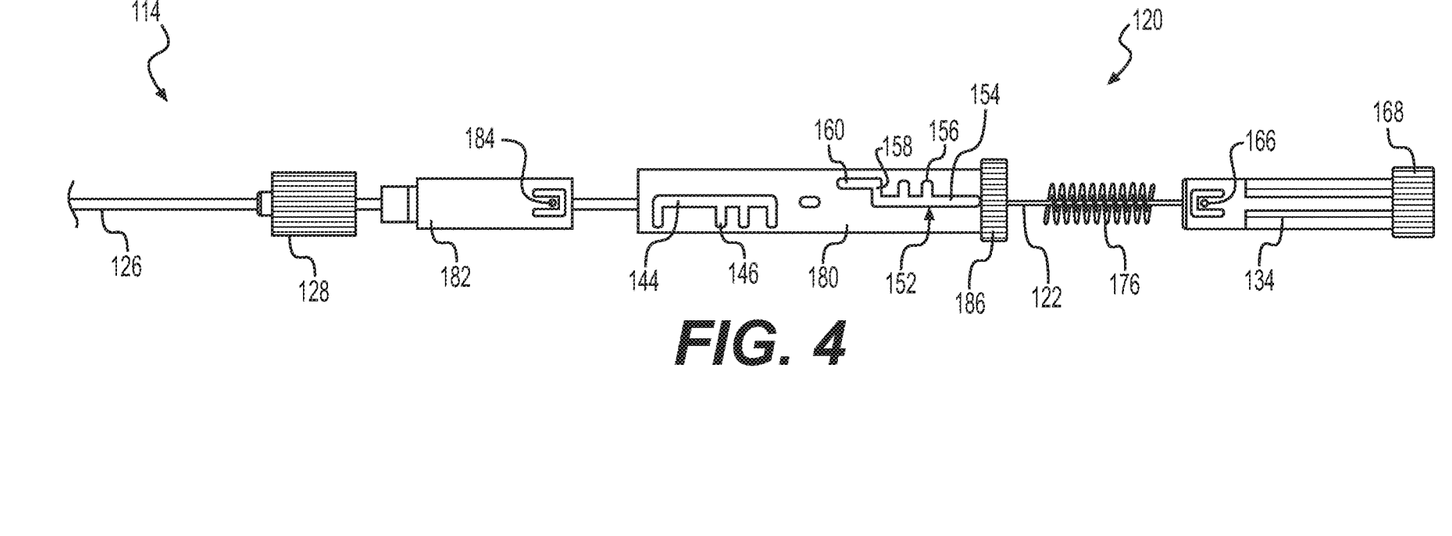
FIG. 4 illustrates an exploded view of an additional exemplary medical device according to aspects of this disclosure.

FIG. 4 illustrates an alternative example with similar elements to the medical device 14 shown by 100 added to the reference numbers. Medical device 114 may include a handle 120 and may be inserted and attached to any insertion device as discussed above by threading or otherwise attaching a cap 128 to a port of the insertion device. The handle 120 of FIG. 4 combines shaft advancement body 30 and channel body 32 of the previous embodiment to form combined body 180 that includes slot track 144 and at least one tab 146 along with channel 152. Channel 152 includes a channel track 154, channel tabs 156, a channel slot 158, and a channel release slot 160. It is noted that the tabs 146 extend in opposite circumferential directions from channel tabs 156 and channel slot 158. It is also noted that combined body 180 includes a narrow central lumen (not shown) in a middle portion of the combined body 180 both to internally attach sheath 126 and to support biasing member 176. Moreover, the shaft 122 may be extended and retracted through action on plunger 134 to move plunger pin 166 relative to channel 152 as discussed above.

As shown in FIG. 4, handle 120 includes a second plunger 182 with a second plunger pin 184. Second plunger 182 may be securely coupled to cap 128 or be integrally formed with cap 128. Combined body 180 includes combined body knob 186. A user may manipulate the combined body knob 186 to manipulate combined body 180 relative to second plunger 182 to move second plunger pin 184 within slot track 144 and tabs 146 in order to selectively position the shaft 122 and sheath 126 relative to the distal end of the insertion device. Then, a user may use plunger knob 168 to manipulate plunger 134 to move plunger pin 166 relative to channel 152 in order to selectively position shaft 122 relative to sheath 126. If shaft 122 is a self-expandable basket, it may expand as it extends from sheath 126 as discussed above.

Figure 5:
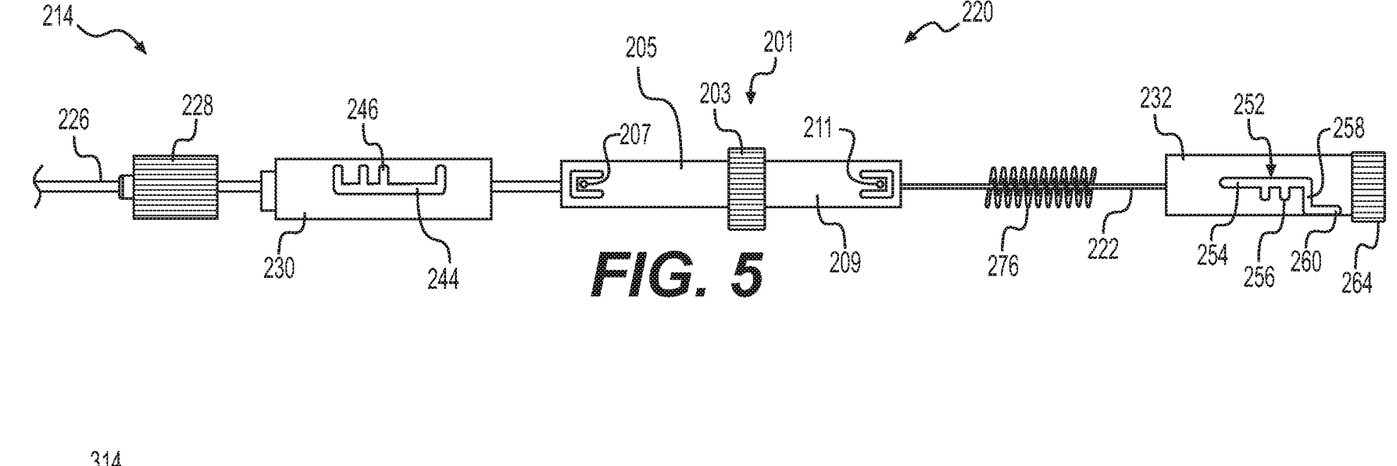
FIG. 5 illustrates an exploded view of an additional exemplary medical device according to aspects of this disclosure.

FIG. 5 illustrates an alternative example with similar elements to the medical device 14 shown by 200 added to the reference numbers. Medical device 214 may include a handle 220 and may be inserted and attached to any insertion device as discussed above by threading or otherwise attaching a cap 228 to a port of the insertion device. The handle 220 of FIG. 5 combines plunger 34 and second plunger 182 of FIG. 4 to be a combined plunger 201. Combined plunger 201 may have a knob 203 in an intermediate portion, a first plunger 205 with first plunger pin 207 in a distal portion, and a second plunger 209 with second plunger pin 211 in a proximal portion. Handle 220 includes a shaft advancement body 230 with a slot track 244 and at least one tab 246 between cap 228 and combined plunger 201. First plunger 205 with first plunger pin 207 may be manipulated to move within shaft advancement body 230 and slot track 244 and the at least one tab 246.

Proximal to combined plunger 201 is channel body 232 with a channel 252 having a channel track 254, at least one channel tab 256, a channel slot 258, and a channel release slot 260. Channel body 232 may also include a channel body knob 264 at a proximal end. It is noted that the channel 252 in this example is substantially similar to the channel 52 in FIGS. 1-4, but with a reversed arrangement of the at least one channel tab 256, channel slot 258, and channel release slot 260. A biasing member 276 may be enclosed by channel body 232 to bias movement of second plunger 209 and channel body 232 relative to each other as second plunger pin 211 is positioned within channel 252.

Sheath 226 may be secured to a narrow channel lumen within combined plunger 201, and shaft 222 may be secured within a narrow proximal lumen of channel body 232. It is noted that the at least one tab 246 extending from slot track 244 in shaft advancement body 230 extends circumferentially opposite to channel tabs 256 and channel slot 258 extending from channel track 254 of channel 252 in channel body 232.

A user may manipulate knob 203 to adjust the position of first plunger 205 within shaft advancement body 230 to move first plunger pin 207 within slot track 244 and at least one tab 246 in order to selectively position the shaft 222 and sheath 226 relative to the distal end of the insertion device 12. Then, a user may manipulate channel body 232 using channel body knob 264 to move channel body 232 relative to second plunger 209 to move second plunger pin 211 within channel 252 in order to selectively position shaft 222 relative to sheath 226. If shaft 222 is a self-expandable basket, it may expand as it extends from sheath 226 as discussed above.

Figure 6:
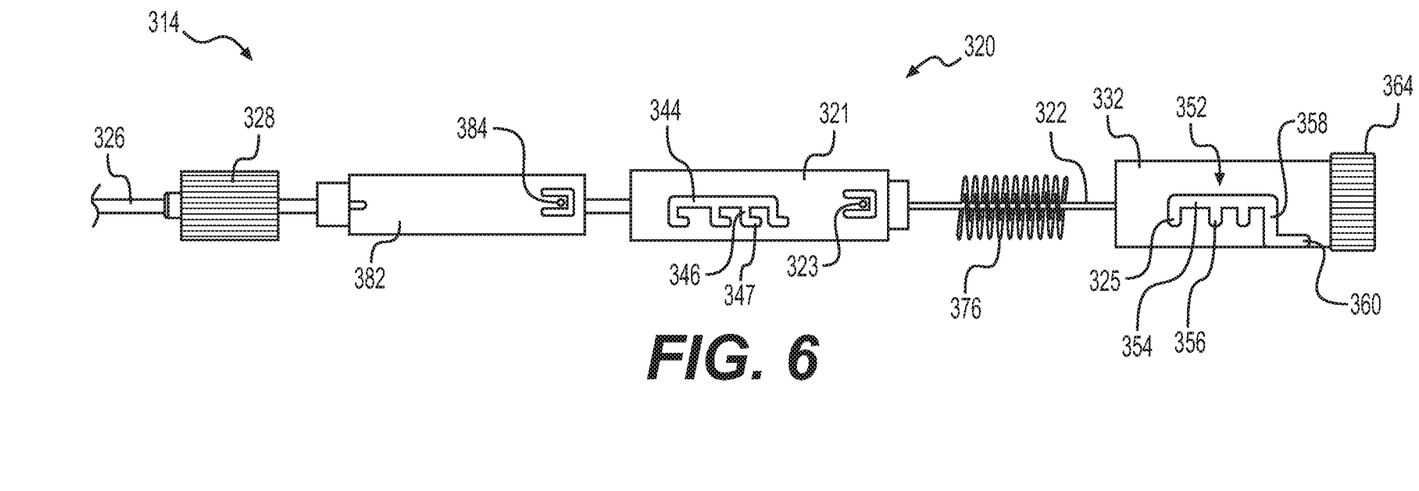
FIG. 6 illustrates an exploded view of an additional exemplary medical device according to aspects of this disclosure.

FIG. 6 illustrates an alternative example with similar elements to the medical device 14 shown by 300 added to the reference numbers. Medical device 314 may include a handle 320 and may be inserted and attached to any insertion device as discussed above by threading or otherwise attaching a cap 328 to a port of the insertion device. The handle 320 of FIG. 6 combines shaft advancement body 30 and plunger 34 of FIGS. 1-3 to form an intermediate body 321. Intermediate body 321 may include a slot track 344 with at least one tab 346 and at least one lock slot 347 in a distal portion of intermediate body 321. Intermediate body 321 may also include a proximal plunger pin 323 in a proximal portion of intermediate body 321. A distal plunger 382 with a distal plunger pin 384 may be positioned between cap 328 and intermediate body 321. Intermediate body 321 or distal plunger 382 may be manipulated to move distal plunger pin 384 within slot track 344, at least one tab 346, and at least one lock slot 347 in intermediate body 321. Although not shown, intermediate body 321 may include a knob to aid in manipulation.

Proximal to intermediate body 321 is channel body 332 with a channel 352 having a channel track 354, at least one channel tab 356, a channel slot 358, and a channel release slot 360. Channel body 332 may also include a channel body knob 364 at a proximal end. It is noted that the channel 352 in this example is substantially similar to the channel 52 in FIGS. 1-3, but with a reversed arrangement of the at least one channel tab 356, channel slot 358, and channel release slot 360 and includes a close tab 325 at a distal most portion of channel track 354. A biasing member 376 may be enclosed by channel body 332 to bias movement of intermediate body 321 and channel body 332 relative to each other as proximal plunger pin 323 is positioned within channel 352.

Sheath 326 may be secured to a narrow channel lumen within intermediate body 321, and shaft 322 may be secured within a narrow proximal lumen of channel body 332. It is noted that the at least one tab 346 extending from slot track 344 in intermediate body 321 extends in the same circumferential direction as channel tabs 356 and channel slot 358 extending from channel track 354 of channel 352 in channel body 332.

A user may manipulate channel body knob 364, with proximal plunger pin 323 in one of the channel tabs 356 or close tab 325, to adjust the position of intermediate body 321 relative to distal plunger 382 such that distal plunger pin 384 is moved within slot track 344, at least one tab 346, and at least one lock slot 347. The position of the intermediate body 321 relative to distal plunger 382 affects the position of the shaft 322 and sheath 326 relative to the distal end of the insertion device. Then, a user may manipulate channel body 332 using channel body knob 364 to move channel body 332 relative to intermediate body 321 to move proximal plunger pin 323 within channel 352 in order to selectively position shaft 322 relative to sheath 326. If shaft 322 is a self-expandable basket, it may expand as it extends from sheath 326 as discussed above.

The disclosed medical devices 14, 114, 214, and 314 and handles 20, 120, 220, and 320 may help enable quick and reliable performance of a medical procedure such as, for example, the capture and removal of a stone or material. For example, with cap 28 secured to port 40 of an insertion device 12, a user may manipulate the position of the shaft 22, the end effector 24, and the sheath 26 relative to the distal end 38 of the delivery shaft 18 of the insertion device with one hand. Additionally, a user may manipulate the position of the shaft 22 and its end effector 24 relative to the sheath using the same one hand. As such, a user may use one hand to manipulate the distal end 38 of the delivery shaft 18 of the insertion device through the handle 20 and deflection lever 36. A user may use another hand to manipulate the medical device 14 as discussed above. Alternatively, medical device 14 may be uncoupled from port 40 and manipulated using two hands or by a different user. Moreover, the distance between, number of, and arrangement of tabs 46 and channel tabs 56 may enable a variety of incremental locked positions for the distal components of insertion device 12 and medical device 14 relative to each other during a medical procedure.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

I claim:

1. A medical device, comprising:
   a sheath;
   a shaft at least partially surrounded by the sheath and movable relative to the sheath;
   an end effector at a distal end of the shaft and movable between at least an open position and a closed position; and
   a handle, the handle including:
   a cap;
   a shaft advancement body fixedly coupled to the cap;
   a channel body securely coupled to the sheath and selectively and lockably positionable with respect to the shaft advancement body to extend or retract the sheath and the shaft relative to the shaft advancement body; and
   a plunger securely coupled to the shaft and selectively and lockably positionable with respect to the channel body to extend or retract the shaft relative to the sheath, wherein the plunger includes a plunger pin positioned on a distal portion of the plunger and formed by a cantilevered protrusion extending radially from the plunger, wherein the plunger pin is movable within a channel in the channel body to move the end effector relative to the sheath between the open position and the closed position,
   wherein the channel includes a longitudinally extending channel track and at least one channel tab extending from the channel track,
   wherein the channel further includes a channel slot and a channel release slot, and
   wherein the channel release slot is connected to the channel track by the channel slot, wherein the channel release slot extends parallel to the channel track, and wherein the channel release slot extends distally beyond the channel track and the channel slot.

2. The medical device of claim 1, wherein the channel body includes a channel pin on a distal portion of the channel body and formed by a cantilevered protrusion extending radially from the channel body, and wherein the channel pin is movable within a slot in the shaft advancement body.

3. The medical device of claim 2, wherein the slot in the shaft advancement body includes at least one tab that extends perpendicular to the slot.

4. The medical device of claim 3, wherein the channel pin is movable within the at least one tab of the slot to secure the channel body in a selected position in the shaft advancement body, and
wherein the position of the channel pin with respect to the shaft advancement body correlates a position of the channel pin with a position of the sheath.

5. The medical device of claim 1, wherein the plunger pin is movable within the at least one channel tab and channel slot to secure the plunger in a selected position in the channel body.

6. The medical device of claim 1, wherein the movement of the plunger within the channel body is urged proximally by a biasing member; and
wherein the biasing member is a compression spring.

7. The medical device of claim 1, wherein the shaft advancement body and the channel body both include slots extending from respective channels on two radially opposing sides of the shaft advancement body and the channel body, and wherein the slots extending from respective channels in the two radially opposing sides of the shaft advancement body and the channel body are mirror images.

8. The medical device of claim 1, wherein the end effector includes an expandable retrieval basket.

9. The medical device of claim 1, wherein the cap is positioned at a distal portion of the handle; and
wherein the cap is internally threaded to form a seal when coupled to a port of an insertion device.

10. The medical device of claim 1, wherein the channel body further includes a radially extending knob at a proximal end; and
wherein the plunger further includes a radially extending plunger knob at a proximal end.

11. A system, comprising:
an insertion device including a body and a delivery shaft with a distal end,
wherein the body includes a port and a deflection lever; and
a medical device including a handle, a shaft at least partially surrounded by a sheath, and an end effector at a distal end of the shaft and movable between at least an open position and a closed position;
wherein the handle includes a cap, a first member, a second member, and a plunger movable relative to one another, the shaft and sheath being controllably movable together and relative to one another when the medical device is coupled to the insertion device, wherein the first member is fixedly coupled to the cap, wherein the second member is securely coupled to the sheath and selectively and lockably positioned with respect to the first member, and wherein the plunger is securely coupled to the shaft and selectively and lockably positionable with respect to the second member,
wherein the second member is movable relative to the first member to position the shaft and the sheath relative to the distal end of the delivery shaft,
wherein the plunger is movable relative to the second member to extend or retract the shaft relative to the sheath, and
wherein movement of the plunger within the second member is urged proximally by a compression spring.

12. The system of claim 11, wherein the shaft and the sheath each have lengths such that when the handle is coupled to the port of the insertion device, the shaft and the sheath are both generally flush with the distal end of the delivery shaft.

13. The system of claim 11, wherein the plunger is rotatable relative to the second member to rotate the shaft relative to the sheath.

14. The system of claim 11, wherein the first body includes a first track and one or more tabs extending perpendicularly from the first track, wherein the second body includes a second track and one or more tabs extending perpendicularly from the second track, wherein the second body includes a pin movable within the first track and the one or more tabs extending from the first track, and wherein the plunger includes a plunger pin movable within the second track and the one or more tabs extending from the second track.

15. The system of claim 14, wherein the pin is positioned on a distal portion of the second body and formed by a cantilevered protrusion extending radially from the second body, and
wherein the plunger pin is positioned on a distal portion of the plunger and formed by a cantilevered protrusion extending radially from the plunger.

16. A medical device, comprising:
a sheath;
a shaft at least partially surrounded by the sheath;
an end effector at a distal end of the shaft and movable between at least an open position and a closed position; and
a handle, wherein the handle includes:
a shaft advancement body, wherein the shaft advancement body includes a first track with at least one tab extending perpendicularly from the first track, and wherein the shaft advancement body includes a second track with at least one tab extending from the second track;
a channel body securely coupled to the sheath and selectively positionable with respect to the shaft advancement body, wherein the channel body includes a first channel pin movable within the first track and the at least one tab in the shaft advancement body, wherein the channel body includes a first channel track with at least one channel tab extending from the first channel track, wherein the channel body includes a second channel pin movable within the second track and the at least one tab extending from the second track in the shaft advancement body, and wherein the channel body includes a second channel track with at least one channel tab extending from the second channel track; and
a plunger securely coupled to the shaft and selectively positionable with respect to the channel body to control the extension of the shaft and the end effector relative to a distal end of the sheath, wherein the plunger includes a first plunger pin movable within the first channel track and the at least one tab in the channel body, and wherein the plunger includes a second plunger pin movable with the second channel slot,
wherein the shaft advancement body and the channel body both include slots extending from respective channels on two radially opposing sides of the shaft advancement body and the channel body, and wherein the slots extending from respective channels in the two radially opposing sides of the shaft advancement body and the channel body are mirror images.

17. The medical device of claim 16, wherein the channel body includes
- a channel slot and a channel release slot, wherein the channel release slot is connected to the first channel track by the channel slot, wherein the channel release slot extends parallel to the first channel track, and wherein the channel release slot extends distally beyond the first channel track and the channel slot,
wherein the plunger pin is movable within the at least one channel tab and the channel slot to secure the plunger in a selected position in the channel body.

* * * * *